United States Patent

Rochus et al.

Patent Number: 6,107,295
Date of Patent: Aug. 22, 2000

[54] ARYLALKANOYL PYRIDAZINES

[75] Inventors: Jonas Rochus, Darmstadt; Norbert Beier, Reinheim; Franz-Werner Kluxen; Michael Wolf, both of Darmstadt, all of Germany

[73] Assignee: Merck Patent Gesellschaft mit Beschrankter Haftung, Germany

[21] Appl. No.: 09/230,801

[22] PCT Filed: Aug. 1, 1997

[86] PCT No.: PCT/EP97/04191

§ 371 Date: Feb. 9, 1999

§ 102(e) Date: Feb. 9, 1999

[87] PCT Pub. No.: WO98/06704

PCT Pub. Date: Feb. 19, 1998

[51] Int. Cl.$^7$ ............... A61K 31/50; C07D 237/04; C07D 401/12; C07D 403/12

[52] U.S. Cl. ............... 514/247; 514/252; 544/224; 544/238

[58] Field of Search .................. 514/247, 252; 544/224, 238

[56] References Cited

U.S. PATENT DOCUMENTS 5,684,151  11/1997  Combs ........................... 544/224

FOREIGN PATENT DOCUMENTS

94/01412  1/1994  WIPO .
9401412   1/1994  WIPO .

OTHER PUBLICATIONS

D. Combs, "Nonsteroidal Progesterone Receptor", Ligands 1.3–Aryl–1–Benzoyl–Tetrahydropyrid Azines, Journal of Medicinal Chemistry, vol. 38, No. 25, 1995, pp. 4878–4879, XP002047380.
WO9401412–English Abstract, Jan. 20, 1994.

Primary Examiner—Fiona T. Powers
Attorney, Agent, or Firm—Millen, White, Zelane, & Branigan, P.C.

[57] ABSTRACT

Arylalkanoylpyridazine derivatives of the formula I

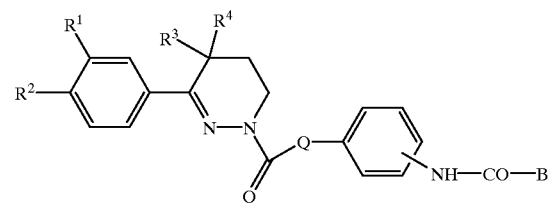

and the physiologically acceptable salts thereof
in which
$R^1$, $R^2$, $R^3$, $R^4$, Q and B have the meanings given in claim 1 act as phosphodiesterase IV inhibitors and can be employed for the treatment of osteoporosis, tumors, atherosclerosis, rheumatoid arthritis, multiple sclerosis, diabetes mellitus, inflammatory processes, allergies, asthma, autoimmune diseases and AIDS.

14 Claims, No Drawings

ARYLALKANOYL PYRIDAZINES

The invention relates to arylalkanoylpyridazine erivatives of the formula I

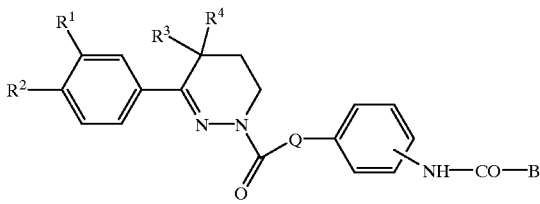

in which
B is A, OA, NH$_2$, NHA, NAA' or an unsaturated heterocycle which has 1 to 4 N, O and/or S atoms and which can be unsubstituted or mono-, di- or trisubstituted by Hal, A and/or OA, Q is absent or is alkylene having 1–6 C atoms, R$^1$, R$^2$ in each case independently of one another are —OH, OR$^5$, —S—R$^5$, —SO—R$^5$, —SO$_2$—R$^5$, Hal, —NO$_2$, —NH$_2$, —NHR$^5$ or —NR$^5$R$^6$, R$^1$ and R$^2$ together are also —O—CH$_2$—O—, R$^3$, R$^4$ in each case independently of one another are H or A, R$^5$, R$^6$ in each case independently of one another are A, cycloalkyl having 3–7 C atoms, methylenecycloalkyl having 4–8 C atoms or alkenyl having 2–8 C atoms, A, A' in each case independently of one another are alkyl which has 1 to 10 C atoms and which can be substituted by 1 to 5 F and/or Cl atoms and Hal is F, Cl, Br or I, and the physiologically acceptable salts thereof.

1-Benzoyltetrahydropyridazines have been described as progesterone receptor ligands, for example in J. Med. Chem. 38, 4878 (1995).

The invention was based on the object of finding novel compounds which have valuable properties, n particular those which can be used for the reparation of pharmaceuticals.

It has been found that the compounds of the formula I and salts thereof have highly valuable harmacological properties and are well tolerated.

In particular, they inhibit selectively phosphodiesterase IV, which causes an increase of the intracellular cAMP level (N.Sommer et al., Nature Medicine, 1, 244–248 (1995)). The PDE IV inhibition can be determined analogously to e.g. C. W. Davis in Biochim. biophys. Acta 797, 354–362 (1984).

The compounds of the formula I can be employed for the treatment of asthmatic diseases. The antiasthmatic activity of PDE IV inhibitors is known from T. J. Torphy et al. in Thorax, 46, 512–523 (1991) and can be determined, for example, by the method of T. Olsson, Acta allergologica 26, 438–447 (1971).

As cAMP inhibits bone decreasing cells and stimulates bone increasing cells (S. Kasugai et al., M681 and K. Miyamoto, M 682, in Abstract of the American Society for Bone and Mineral Research 18$^{th}$ annual meeting 1996), the compounds of formula I can be employed for the treatment of osteoporosis.

Moreover, the compounds have an inhibitory effect on the formation of TNF (tumor necrosis factor) and are therefore suitable for the treatment of allergies and inflammatory diseases, autoimmune diseases and transplant rejection reactions. They can furthermore be used for the treatment of dysmnesia, tumors, atherosclerosis, rheumatoid arthritis, multiple sclerosis, Morbus Crohn, atopic dermatitis, diabetes mellitus, ulcerative colitis and AIDS.

PDE IV inhibitors are potent compounds for the treatment of asthmatic and inflammatory diseases, diabetes mellitus, atopic dermatitis, psoriasis, AIDS, tumor growth or tumor metastasis (see e.g. EP 77 92 91).

The antiinflammatory effect of the compounds of the formula I and their potency for the treatment of e.g. autoimmune diseases, multiple sclerosis or rheumatoid arthritis can be determined analogously to the methods of N. Sommer et al., Nature Medicine, 1, 244–248 (1995) or L. Sekut et al., Clin. Exp. Immunol., 100, 126–132 (1995).

PDE IV inhibitors are effective in the treatment of tumors (see e.g. WO 95 35 281, WO 95 17 399 or WO 96 00 215) The compounds of the formula I can be employed as pharmaceutically active ingredients in human and veterinary medicine. Furthermore, they can be employed as intermediates for the preparation of other pharmaceutically active ingredients.

Accordingly, the invention relates to the compounds of the formula I and to a process for the preparation of compounds of the formula I according to claim 1 and salts thereof, characterized in that a compound of the formula II

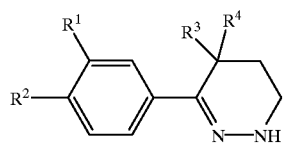

in which R$^1$, R$^2$, R$^3$ and R$^4$ have the abovementioned meanings
is reacted with a compound of the formula III

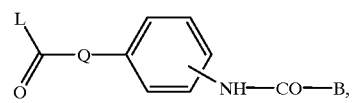

in which
B and Q have the abovementioned meanings and L is Cl, Br, OH or a reactive esterified OH group, or
in that a compound of the formula IV

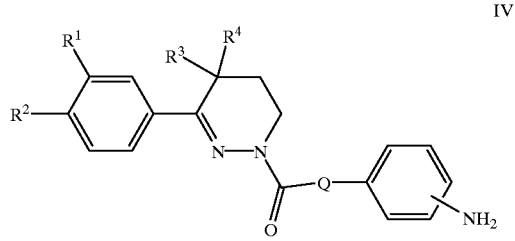

in which $R^1$, $R^2$, $R^3$, $R^4$ and Q have the abovementioned meanings is reacted with a compound of the formula V

  B—CO—L    V in which

B has the abovementioned meaning and

L is Cl, Br, OH or a reactive esterified OH group, and/or in that a basic compound of the formula I is converted into a salt thereof by treatment with an acid.

The radicals, $R^1$, $R^2$, $R^3$, $R^4$, B, Q and L hereinabove and hereinbelow have the meanings given for the formulae I, II, III, IV and V, unless expressly stated otherwise.

Compounds of the formula I can be chiral and can accordingly occur in different isomeric forms. All these forms (e.g. R- and S-forms) and their mixtures (e.g. the R,S-forms) are embraced by the formula I.

A and A' are by preference alkyl, further preferably alkyl which is substituted by 1 to 5 fluorine and/or chlorine atoms.

In the above formulae, alkyl is by preference unbranched and has 1, 2, 3, 4, 5, 6, 7, 8, 9 or 10 C atoms, by preference 1, 2, 3, 4 or 5 C atoms, and is by preference methyl, ethyl, trifluoromethyl, pentafluoroethyl or propyl, furthermore preferably isopropyl, butyl, isobutyl, sec-butyl or tert-butyl, but also n-pentyl, neo-pentyl or isopentyl.

Cycloalkyl has by preference 3–7 C atoms and is preferably cyclopropyl and cyclobutyl, furthermore preferably cyclopentyl or cyclohexyl, furthermore also cycloheptyl.

Methylenecycloalkyl has by preference 4–8 C atoms and is preferably methylenecyclopropyl and methylenecyclobutyl, furthermore preferably methylenecyclopentyl and methylenecyclohexyl, furthermore also methylenecycloheptyl.

Alkenyl is by preference vinyl, 1- or 2-propenyl, 1-butenyl, isobutenyl, sec-butenyl, and is furthermore preferably 1-pentenyl, isopentenyl or 1-hexenyl.

Alkylene is by preference unbranched and is preferably methylene or ethylene, furthermore preferably propylene or butylene.

Of the radicals $R^3$ and $R^4$, one is preferably H, while the other is preferably propyl or butyl, but particularly preferably ethyl or methyl. Furthermore, $R^1$ and $R^2$ together are also preferably each hydrogen.

Hal is by preference F, Cl or Br, but also I.

The radicals $R^1$ and $R^2$ can be identical or different and are in the 3- or 4-position of the phenyl ring. For example, they are independently of one another hydroxyl, —S—$CH_3$, —SO—$CH_3$, —$SO_2CH_3$, F, Cl, Br or I or together methylenedioxy. However, especially preferably they are in each case methoxy, ethoxy, propoxy, cyclopentoxy, or else fluoro-, difluoro- or trifluoromethoxy, 1-fluoro-, 2-fluoro-, 1,2-difluoro-, 2,2-difluoro-, 1,2,2-trifluoro- or 2,2,2-trifluoroethoxy.

The radical B is by preference 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzoisoxazolyl, 2-, 4-, 5-, 6- or 7-benzothiazolyl, 2-, 4-, 5-, 6- or 7-benzoisothiazolyl, 4-, 5-, 6- or 7-benzo-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

The radical B is furthermore by preference methyl, ethyl, propyl, n-butyl, methoxy, ethoxy, propoxy, N-methylamino, N,N-dimethylamino, N-ethylamino or N,N-diethylamino.

The rule that all radicals which occur more than once can be identical or different, that is to say are independent of one another, applies to the entire invention.

Accordingly, the invention relates in particular to those compounds of the formula I in which at least one of the abovementioned radicals has one of the preferred meanings given above. Some preferred groups of compounds can be expressed by the following subformulae Ia to Ie which correspond to the formula I and in which radicals which are not defined in greater detail have the meanings given for the formula I, but where in Ia, $R^1$ and $R^2$ are in each case independently of one another OA, Q is absent and B is pyridinyl, pyrazinyl, pyrimidinyl, thiazolyl, imidazolyl or isoxazolyl;

in Ib, $R^1$ and $R^2$ in each case independently of one another are OA,

Q is methylene and

B is pyridinyl, pyrazinyl, pyrimidinyl, thiazolyl, imidazolyl or isoxazolyl;

in Ic, $R^1$ and $R^2$ together are —O—$CH_2$—O—,

Q is absent or alkylene with 1–6 C atoms and

B is pyridinyl, pyrazinyl, pyrimidinyl, thiazolyl, imidazolyl or isoxazolyl;

in Id, $R^1$ and $R^2$ in each case independently of one another are OA,

Q is absent or alkylene with 1–6 C atoms and

B is A or OA;

in Ie, $R^1$ and $R^2$ are in each case independently of one another OA,

Q is absent or alkylene with 1–6 C atoms,

B is pyridinyl, pyrazinyl, pyrimidinyl, thiazolyl, imidazolyl, isoxazolyl, A, OA or $NH_2$.

Besides, the compounds of the formula I and also the starting materials for their preparation are prepared by methods known per se as they are described in the literature (for example in the standard publications such as Houben-Weyl, Methoden der organischen Chemie [Methods in organic chemistry], Georg-Thieme-Verlag, Stuttgart), under reaction conditions which are known and suitable for the abovementioned reactions. It is also possible to utilize variants which are known per se but are not mentioned in greater detail in the present text.

In the compounds of the formulae II and IV, $R^1$, $R^2$, $R^3$, $R^4$ and Q have the abovementioned meanings, in particular the abovementioned preferred meanings.

In the compounds of the formulae III and IV, Q is by preference methylene or ethylene, furthermore preferably propylene or butylene.

B in the compounds of the formulae III and V has the abovementioned preferred meanings, while L is Cl, Br, OH or a reactive esterified OH group.

If L is a reactive esterified OH group, it is by preference alkylsulfonyloxy having 1–6 C atoms (preferably methylsulfonyloxy) or arylsulfonyloxy having 6–10 C atoms (preferably phenyl- or p-tolylsulfonyloxy, furthermore also 2-naphthalenesulfonyloxy).

If desired, the starting materials can also be formed in situ, so that they are not isolated from the reaction mixture but immediately reacted further to give the compounds of the formula I. On the other hand, it is possible to carry out the reaction stepwise.

By preference, the compounds of the formula I can be obtained by reacting compounds of the formula II with compounds of the formula III.

Some of the starting materials of the formulae II and III are known. If they are not known, they can be prepared by methods known per se. In detail, the reaction of the compounds of the formula II with the compounds of the formula III is carried out in the presence or absence of an inert solvent at temperatures between approximately −20 and approximately 150°, preferably between 20 and 100°.

Examples of suitable inert solvents are hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl ether, ethylene glycol monoethyl ether (methyl glycol or ethyl glycol), ethylene glycol dimethyl ether (diglyme); ketones such as acetone or butanone; amides such as acetamide, dimethylacetamide or dimethylformamide (DMF); nitrites such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, or mixtures of the abovementioned solvents.

Moreover, compounds of the formula I can be obtained by reacting compounds of the formula IV with compounds of the formula V. As a rule, the starting compounds of the formulae IV and V are known. If they are not known, they can be prepared by methods known per se. Thus, for example, the preparation of 1-benzoyltetrahydropyridazine is described in J. Med. Chem. 38, 4878 (1995).

In the compounds of the formula V, the radical —CO—L is a pre-activated carboxylic acid, preferably a carboxylic acid halide.

The compounds of the formula IV are reacted with compounds of the formula V under the same conditions regarding reaction time, temperature and solvent as has been described for the reaction of the compounds of the formula II with compounds of the formula III.

A base of the formula I can be converted into the corresponding acid addition salt with an acid, for example by reacting equivalent amounts of the base and the acid in an inert solvent such as ethanol, followed by evaporation. Acids which are suitable for this reaction are, in particular, those which give physiologically acceptable salts. Thus, inorganic acids can be used, for example sulfuric acid, nitric acid, hydrohalic acids such as hydrochloric acid or hydrobromic acid, phosphorus acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfonic acid. Salts with acids which are physiologically not acceptable, for example picrates, can be used for isolating and/or purifying the compounds of the formula I.

On the other hand, the free bases of the formula I can be liberated from their salts using bases (for example sodium hydroxide, sodium carbonate, potassium hydroxide or potassium carbonate), if so desired.

The invention furthermore relates to the use of the compounds of the formula I and/or of the physiologically acceptable salts thereof for the preparation of pharmaceutical products, in particular via the non-chemical route. They can be brought into a suitable pharmaceutical form together with at least one solid, liquid and/or semi-liquid excipient or auxiliary and, if appropriate, in combination with one or more further active ingredients.

The invention also relates to pharmaceuticals of the formula I and to the physiologically acceptable salts thereof as phosphodiesterase IV inhibitors.

The invention furthermore relates to pharmaceutical products comprising at least one compound of the formula I and/or a physiologically acceptable salt thereof.

These products can be used as pharmaceuticals in human or veterinary medicine. Suitable excipients are organic or inorganic substances which are suitable for enteral (for example oral), parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc, petroleum jelly. Pharmaceutical forms which are used for oral administration are, in particular, tablets, pills, sugar-coated tablets, capsules, powders, granules, syrups, liquids or drops; pharmaceutical forms which can be used, in particular, for rectal administration are suppositories; pharmaceutical forms which can be used for parenteral administration are, in particular, solutions, preferably oily or aqueous solutions, furthermore suspensions, emulsions or implants, and pharmaceutical forms which can be used for topical administration are, in particular, ointments, creams or powders. The novel compounds can also be lyophilized and the resulting lyophilizates used for example for the preparation of injectable products. The abovementioned products can be sterilized and/or comprise auxiliaries such as glidants, preservatives, stabilizers and/or wetting agents, emulsifiers, salts for modifying the osmotic pressure, buffer substances, colours, flavourings and/or a plurality of other active ingredients, for example one or more vitamins.

The compounds of the formula I and their physiologically acceptable salts can be employed for combating diseases where a raised cAMP (cyclo-adenosine monophosphate) level leads to the inhibition or prevention of inflammations and to muscular relaxation. The compounds according to the invention can be used especially in the treatment of allergies, asthma, chronic bronchitis, atopic dermatitis, psoriasis and other skin diseases and autoimmune diseases.

In this connection, the substances according to the invention are generally preferably administered in doses of between approximately 1 and 500 mg, in particular of between 5 and 100 mg per dose unit. The daily dose is preferably between approximately 0.02 and 10 mg/kg of body weight. The specific dose for each patient, however, depends on all sorts of factors, for example on the efficacy of the specific compound employed, on the age, body weight, general state of health, sex, on the diet, on the time and route of administration, and on the excretion rate, pharmaceutical substance combination and severity of the particular disorder to which the therapy applies. Oral administration is preferred.

All temperatures hereinabove and hereinbelow are given in ° C. In the examples which follow, "customary work-up" means: if required, water is added; if required, the pH is brought to between 2 and 10, depending on the constitution of the end product; the mixture is extracted with ethyl acetate or dichloromethane and separated; the organic phase is dried over sodium sulfate and evaporated; and the residue is purified by chromatography on silica gel and/or by crystallization.

Mass spectrometry (MS): EI(electron impact ionization) M+FAB (fast atom bombardment)(M+H)$^+$

EXAMPLE 1

A suspension of 4.70 g of 3-(3,4-dimethoxyphenyl)-1,4,5,6-tetrahydropyridazine ("A") in 150 ml of THF is treated with 2.24 g of potassium tert-butoxide and the mixture is stirred for 30 minutes. 7.3 g of 4-nicotinoylaminobenzoyl chloride are added, and stirring is continued for 10 hours at room temperature. The solvent is removed and the mixture is worked up as customary. This gives 1-(4-nicotinoylaminobenzoyl)-3-(3,4-dimethoxyphenyl)-1,4,5,6-tetrahydropyridazine hydrochloride, m.p. 239° (decomposition).

The following is obtained analogously by reaction of "A" with 4-isonicotinoylaminobenzoyl chloride: 1-(4-isonicotinoylaminobenzoyl)-3-(3,4-dimethoxyphenyl)-1,4,5,6-tetrahydropyridazine hydrochloride, m.p. 247° (decomposition).

EXAMPLE 2

A solution of 2.0 g of 1-(4-aminobenzoyl)-3-(3,4-dimethoxyphenyl)-1,4,5,6-tetrahydropyridazine, m.p. 197° [obtainable by catalytic hydrogenation of 1-(4-nitrobenzoyl)-3-(3,4-dimethoxyphenyl)-1,4,5,6-tetrahydropyridazine, m.p. 203° in 150 ml of tetrahydrofuran in the presence of 3.5 g of Raney nickel at room temperature] and 1.6 ml of pyridine in 150 ml of acetonitrile is treated with 1.2 g of nicotinoyl chloride hydrochloride and stirring is continued for two hours. The solvent is removed and the residue is worked up as customary. After recrystallization, 1-(4-nicotinoylaminobenzoyl)-3-(3,4-dimethoxyphenyl)-1,4,5,6-tetrahydropyridazine hydrochloride, m.p. 239° (decomposition), is obtained.

The compounds given further below are obtained analogously by reacting the "amine derivatives" which follow 1-(3-aminobenzoyl)-3-(3,4-dimethoxyphenyl)-1,4,5,6-tetrahydropyridazine, m.p. 168°;

1-(2-aminobenzoyl)-3-(3,4-dimethoxyphenyl)-1,4,5,6-tetrahydropyridazine, 1-(4-aminobenzoyl)-3-(3-ethoxy-4-methoxyphenyl)-1,4,5,6-tetrahydropyridazine, m.p. 154°;

1-(3-aminobenzoyl)-3-(3-ethoxy-4-methoxyphenyl)-1,4,5,6-tetrahydropyridazine, 1-(4-aminobenzoyl)-3-(3-cyclopentyloxy-4-methoxyphenyl)-1,4,5,6-tetrahydropyridazine, m.p. 168°;

1-(3-aminobenzoyl)-3-(3-cyclopentyl-4-methoxyphenyl)-1,4,5,6-tetrahydropyridazine, 1-(4-aminobenzoyl)-3-(3,4-methylenedioxyphenyl)-1,4,5,6-tetrahydropyridazine, 1-(4-aminobenzoyl)-3-(3-methoxy-4-methylsulfonylphenyl)-1,4,5,6-tetrahydropyridazine, 1-(4-aminobenzoyl)-3-(3-trifluoromethoxy-4-methoxyphenyl)-1,4,5,6-tetrahydropyridazine, with nicotinoyl chloride:

1-(3-nicotinoylaminobenzoyl)-3-(3,4-dimethoxyphenyl)-1,4,5,6-tetrahydropyridazine hydrochloride, 159° (decomposition);

1-(2-nicotinoylaminobenzoyl)-3-(3,4-dimethoxyphenyl)-1,4,5,6-tetrahydropyridazine, 1-(4-nicotinoylaminobenzoyl)-3-(3-ethoxy-4-methoxyphenyl)-1,4,5,6-tetrahydropyridazine, 1-(3-nicotinoylaminobenzoyl)-3-(3-ethoxy-4-methoxyphenyl)-1,4,5,6-tetrahydropyridazine hydrochloride, 235°, 1-(4-nicotinoylaminobenzoyl)-3-(3-cyclopentyloxy-4-methoxyphenyl)-1,4,5,6-tetrahydropyridazine hydrochloride, m.p. 224° (decomposition);

1-(3-nicotinoylaminobenzoyl)-3-(3-cyclopentyloxy-4-methoxyphenyl)-1,4,5,6-tetrahydropyridazine, 1-(4-nicotinoylaminobenzoyl)-3-(3,4-methylenedioxyphenyl)-1,4,5,6-tetrahydropyridazine, 1-(4-nicotinoylaminobenzoyl)-3-(3-methoxy-4-methylsulfonylphenyl)-1,4,5,6-tetrahydropyridazine, 1-(4-nicotinoylaminobenzoyl)-3-(3-trifluoromethoxy-4-methoxyphenyl)-1,4,5,6-tetrahydropyridazine.

The compounds which follow are obtained analogously by reacting the "amine derivatives" listed above with isonicotinoyl chloride:

1-(4-isonicotinoylaminobenzoyl)-3-(3,4-dimethoxyphenyl)-1,4,5,6-tetrahydropyridazine, m.p. 247° (decomposition);

1-(3-isonicotinoylaminobenzoyl)-3-(3,4-dimethoxyphenyl)-1,4,5,6-tetrahydropyridazine hydrochloride, 175° (decomposition);

1-(2-isonicotinoylaminobenzoyl)-3-(3,4-dimethoxyphenyl)-1,4,5,6-tetrahydropyridazine, 1-(4-isonicotinoylaminobenzoyl)-3-(3-ethoxy-4-methoxyphenyl)-1,4,5,6-tetrahydropyridazine hydrochloride, m.p. 266°;

1-(3-isonicotinoylaminobenzoyl)-3-(3-ethoxy-4-methoxyphenyl)-1,4,5,6-tetrahydropyridazine, 1-(4-isonicotinoylaminobenzoyl)-3-(3-cyclopentyloxy-4-methoxyphenyl)-1,4,5,6-tetra-hydropyridazine hydrochloride, m.p. 244° (decomposition);

1-(3-isonicotinoylaminobenzoyl)-3-(3-cyclopentyloxy-4-methoxyphenyl)-1,4,5,6-tetrahydropyridazine, 1-(4-isonicotinoylaminobenzoyl)-3-(3,4-methylenedioxyphenyl)-1,4,5,6-tetrahydropyridazine, 1-(4-isonicotinoylaminobenzoyl)-3-(3-methoxy-4-methylsulfonylphenyl)-1,4,5,6-tetrahydropyridazine, 1-(4-isonicotinoylaminobenzoyl)-3-(3-trifluoromethoxy-4-methoxyphenyl)-1,4,5,6-tetrahydropyridazine.

The compounds which follow are obtained analogously by reacting the "amine derivatives" listed above with picolinoyl chloride:

1-(4-picolinoylaminobenzoyl)-3-(3,4-dimethoxyphenyl)-1,4,5,6-tetrahydropyridazine, 1-(3-picolinoylaminobenzoyl)-3-(3,4-dimethoxyphenyl)-1,4,5,6-tetrahydropyridazine, 1-(2-(picolinoylaminobenzoyl)-3-(3,4-dimethoxyphenyl)-1,4,5,6-tetrahydropyridazine, 1-(4-picolinoylaminobenzoyl)-3-(3-ethoxy-4-methoxyphenyl)-1,4,5,6-tetrahydrc,pyridazine, 1-(3-picolinoylaminobenzoyl)-3-(3-ethoxy-4-methoxyphenyl)-1,4,5,6-tetrahydropyridazine, 1-(4-picolinoylaminobenzoyl)-3-(3-cyclopentyloxy-4-methoxyphenyl)-1,4,5,6-tetrahyropyridazine, 1-(3-picolinoylaminobenzoyl)-3-(-cyclopentyloxy-4-methoxyphenyl)-1,4,5,6-tetrahyropyridazine, 1-(4-picolinoylaminobenzoyl)-3-(3,4,-methylenedioxyphenyl)-1,4,5,6-tetrahydropyridazine, 1-(4-picolinoylaminobenzoyl)-3-(3-methoxy-4-methylsulfonylphenyl)-1,4,5,6-tetrahydropyridazine, 1-(4-picolinoylaminobenzoyl)-3-(3-trifluoromethoxy-4-methoxyphenyl)-1,4,5,6-tetrahydropyridazine.

The compounds which follow are obtained analogously by reacting the "amine derivatives" listed above with furan-2-carbonyl chloride:

1-(4-(furan-2-carbonylamino)benzoyl)-3-(3,4-dimethoxyphenyl)-1,4,5,6-tetrahydropyridazine, 1-(3-(furan-2-carbonylamino)benzoyl)-3-(3,4-dimethoxyphenyl)-1,4,5,6-tetrahydropyridazine, 1-(2-(furan-2-carbonylamino)benzoyl)-3-(3,4-dimethoxyphenyl)-1,4,5,6-tetrahydropyridazine, 1-(4-(furan-2-carbonylamino)benzoyl)-3-(3-ethoxy-4-methoxyphenyl)-1,4,5,6-tetrahydropyridazine, 1-(3-(furan-2-carbonylamino)benzoyl)-3-(3-ethoxy-4-methoxyphenyl)-1,4,5,6-tetrahydropyridazine, 1-(4-(furan-2-carbonylamino)benzoyl)-3-(3-cyclopentyloxy-4-methoxyphenyl)-1,4,5,6-tetrahydropyridazine, 1-(3-(furan-2-carbonylamino)benzoyl)-3-(3-cyclopentyloxy-4-methoxyphenyl)-1,4,5,6-tetrahydropyridazine, 1-(4-(furan-2-carbonylamino)benzoyl)-3-(3,4-methylenedioxyphenyl)-1,4,5,6-tetrahydropyridazine, 1-(4-(furan-2-carbonylamino)benzcyl)-3-(3-methoxy-4-methylsulfonylphenyl)-1,4,5,6-tetrahydropyridazine, 1-(4-(furan-2-carbonylamino)benzoyl)-3-(3-trifluoromethoxy-4-methoxyphenyl)-1,4,5,6-tetrahydropyridazine.

The compounds which follow are obtained analogously by reacting the "amine derivatives" listed above with thiophene-2-carbonyl chloride:

1-(4-thiophene-2-carbonylamino)benzoyl)-3-(3,4-dimethoxyphenyl)-1,4,5,6-tetrahydropyridazine, 1-(3-(thiophene-2-carbonylamino)benzoyl)-3-(3,4-dimethoxyphenyl)-1,4,5,6-tetrahydopyridazine, 1-(2-(thiophene-2-carbonylamino)benzoyl)-3-(3,4-dimethoxyphenyl)-1,4,5,6-tetrahydropyridazine, 1-(4-(thiophene-2-carbonylamino)benzoyl)-3-(3-ethoxy-4-methoxyphenyl)-1,4,5,6-tetrahydropyridazine, 1-(3-(thiophene-2-carbonylamino)benzoyl)-3-(3-ethoxy-4-methoxyphenyl)-1,4,5,6-tetrahydropyridazine, 1-(4-(thiophene-2-carbonylamino)benzoyl)-3-(3-cyclopentyloxy-4-methoxyphenyl)-1,4,5,6-tetrahydropyridazine, 1-(3-(thiophene-2-carbonylamino)benzoyl)-3-(3-cyclopentyloxy-4-methoxyphenyl)-1,4,5,6-tetrahydropyridazine, 1-(4-(thiophene-2-carbonylamino)benzoyl)-3-(3,4-methylenedioxyphenyl)-1,4,5,6-tetrahydropyridazine, 1-(4-(thiophene-2-carbonylamino)benzoyl)-3-(3-methoxy-4-methylsulfonylphenyl)-1,4,5,6-tetrahydropyridazine, 1-(4-(thiophene-2-carbonylamino)benzoyl)-3-(3-trifluoromethoxy-4-methoxyphenyl)-1,4,5,6-tetrahydropyridazine.

The compounds which follow are obtained analogously by reacting the "amine derivatives" listed above with pyrazine-2-carbonyl chloride:

1-(4-pyrazine-2-carbonylamino)benzoyl)-3-(3,4-dimethoxyphenyl)-1,4,5,6-tetrahydropyridazine, m.p. 213°;

1-(3-(pyrazine-2-carbonylamino)benzoyl)-3-(3,4-dimethoxyphenyl)-1,4,5,6-tetrahydropyridazine, m.p. 204°;

1-(2-(pyrazine-2-carbonylamino)benzoyl)-3-(3,4-dimethoxyphenyl)-1,4,5,6-tetrahydropyridazine, 1-(4-(pyrazine-2-carbonylamino)benzoyl)-3-(3-ethoxy-4-methoxyphenyl)-1,4,5,6-tetrahydropyridazine, m.p. 186°;

1-(3-(pyrazine-2-carbonylamino)benzoyl-3-(3-ethoxy-4-methoxyphenyl)-1,4,5,6-tetrahydropyridazine, 1-(4-(pyrazine-2-carbonylamino)benzoyl)-3-(3-cyclopentyloxy-4-methoxyphenyl)-1,4,5,6-tetrahydropyridazine, m.p. 225°;

1-(3-(pyrazine-2-carbonylamino)benzoyl)-3-(3-cyclopentyloxy-4-methoxyphenyl)-1,4,5,6-tetrahydropyridazine, 1-(4-(pyrazine-2-carbonylamino)benzoyl)-3-(3,4-methylenedioxyphenyl)-1,4,5,6-tetrahydropyridazine, 1-(4-(pyrazine-2-carbonylamino)benzoyl)-3-(3-methoxy-4-methylsulfonylphenyl)-1,4,5,6-tetrahydropyridazine, 1-(4-(pyrazine-2-carbonylamino)benzoyl)-3-(3-trifluoromethoxy-4-methoxyphenyl)-1,4,5,6-tetrahydropyridazine.

The compounds which follow are obtained analogously by reacting the "amine derivatives" listed above with imidazole-4-carbonyl chloride:

1-(4-imidazole-4-carbonylamino)benzoyl)-3-(3,4-dimethoxyphenyl)-1,4,5,6-tetrahydropyridazine, 1-(3-imidazole-4-carbonylamino)benzoyl)-3-(3,4-dimethoxyphenyl)-1,4,5,6-tetrahydropyridazine, 1-2-(imidazole-4-carbonylamino)benzoyl)-3-(3,4-dimethoxyphenyl)-1,4,5,6-tetrahydropyridazine, 1-(4-(imidazole-4-carbonylamino)benzoyl)-3-(3-ethoxy-4-methoxyphenyl)-1,4,5,6-tetrahydropyridazine, 1-(3-(imidazole-4-carbonylamino)benzoyl)-3-(3-ethoxy-4-methoxyphenyl)-1,4,5,6-tetrahydropyridazine, 1-(4-(imidazole-4-carbonylamino)benzoyl)-3-(3-cyclopentyloxy-4-methoxyphenyl)-1,4,5,6-tetrahydropyridazine, 1-(3-(imidazole-4-carbonylamino)benzoyl)-3-(3-cyclopentyloxy-4-methoxyphenyl)-1,4,5,6-tetrahydropyridazine, 1-(4-(imidazole-4-carbonylamino)benzoyl)-3-(3,4-methylenedioxyphenyl)-1,4,5,6-tetrahydropyridazine, 1-(4-imidazole-4-carbonylamino)benzoyl)-3-(3-methoxy-4-methylsulfonylphenyl)-1,4,5,6-tetrahydropyridazine, 1-(4-(imidazole-4-carbonylamino)benzoyl)-3-(3-trifluoromethoxy-4-methoxyphenyl.

The compounds which follows are obtained analogously by reacting the "amine derivatives" listed above with 2,4-dimethylthiazole-5-carbonyl chloride:

1-(4-(2,4-dimethylthiazole-5-carbonylamino)benzoyl)-3-(3,4-dimethoxyphenyl)-1,4,5,6-tetrahydropyridazine, 1-(3-(2,4-dimethylthiazole-5-carbonylamino)benzoyl)-3-(3,4-dimethoxyphenyl)-1,4,5,6-tetrahydropyridazine, 1-(2-(2,4-dimethylthiazole-5-carbonylamino)benzoyl)-3-(3,4-dimethoxyphenyl)-1,4,5,6-tetrahydropyridazine, 1-(4-(2,4-dimethylthiazole-5-carbonylamino)benzoyl)-3-(3-ethoxy-4-methoxyphenyl)-1,4,5,6-tetrahydropyridazine, 1-(3-(2,4-dimethylthiazole-5-carbonylamino)benzoyl)-3-(3-ethoxy-4-methoxyphenyl)-1,4,5,6-tetrahydropyridazine, 1-(4-(2,4-dimethylthiazole-5-carDonylamino)benzoyl)-3-(3-cyclopentyloxy-4-methoxyphenyl)-1,4,5,6-tetrahydropyridazine, 1-(3-(2,4-dimethylthiazole-5-carbonylamino)benzoyl)-3-(3-cyclopentyloxy-4-methoxyphenyl)-1,4,5,6-tetrahydropyridazine, 1-(4-(2,4-dimethylthiazole-5-carbonylamino)benzoyl)-3-(3,4-methylenedioxyphenyl)-1,4,5,6-tetrahydropyridazine, 1-(4-(2,4-dimethylthiazole-5-carbonylamino)benzoyl)-3-(3-methoxy-4-methylsulfonpylphenyl)-1,4,5,6-tetrahydropyridazine, 1-(4-(2,4-dimethylthiazole-5-carbonylamino)benzoyl)-3-(3-trifluoromethoxy-4-methoxyphenyl)-1,4,5,6-tetrahydropyridazine.

The compounds which follow are obtained analogously by reacting the "amine derivatives" listed above with isoxazole-5-carbonyl chloride:

1-(4-(isoxazole-5-carbonylamino)benzoyl)-3-(3,4-dimethoxyphenyl)-1,4,5,6-tetrahydropyridazine, 1-(3-(isoxazole-5-carbonylamino)benzoyl)-3-(3,4-dimethoxyphenyl)-1,4,5,6-tetrahydropyridazine, 1-(2-(isoxazole-5-carbonylamino)benzoyl)-3-(3,4-dimethoxyphenyl)-1,4,5,6-tetrahydrcpyridazine, 1-(4-(isoxazole-5-carbonylamino)-3-(3-ethoxy-4-methoxyphenyl)-1,4,5,6-tetrahydropyridazine, 1-(3-(isoxazole-5-carbonylamino)benzoyl)-3-(3-ethoxy-4-methoxyphenyl)-1,4,5,6-tetrahydropyridazine, 1-(4-(isoxazole-5-carbonylamino)benzoyl)-3-(3-cyclopentyloxy-4-methoxyphenyl)-1,4,5,6-tetrahydropyridazine, 1-(3-(isoxazole-5-carbonylamino)benzoyl)-3-(3-cyclopentyloxy-4-methoxyphenyl)-1,4,5,6-tetrahydropyridazine, 1-(4-(isoxazole-5-carbonylamino)benzoyl)-3-(3,4-methylenedioxyphenyl)-1,4,5,6-tetrahydropyridazine, 1-(4-(isoxazole-5-carbonylamino)benzoyl)-3-(3-methoxy-4-methylsulfonylphenyl)-1,4,5,6-tetrahydropyridazine, 1-(4-(isoxazole-5-carbonylamino)benzoyl)-3-(3-trifluoromethoxy-4-methoxyphenyl)-1,4,5,6-tetrahydropyridazine.

The compounds which follow are obtained analogously by reacting the "amine derivatives" listed above with pyrimidine-2-carbonyl chloride:

1-(4-(pyrimidine-2-carbonylamino)benzoyl)-3-(3,4-dimethoxyphenyl)-1,4,5,6-tetrahydropyridazine, 1-(3-(pyrimidine-2-carbonylamino)benzoyl)-3-(3,4-dimethoxyphenyl)-1,4,5,6-tetrahydropyridazine, 1-(2-(pyrimidine-2-carbonylamino)benzoyl)-3-(3,4-dimethoxyphenyl)-1,4,5,6-tetrahydrc)pyridazine, 1-(4-(pyrimidine-2-carbonylamino)benzoyl)-3-(3-ethoxy-4-methoxyphenyl)-1,4,5,6-telrahydropyridazine, 1-(3-(pyrimidine-2-carbonylamino)benzoyl)-3-(3-ethoxy-4-methoxyphenyl)-1,4,5,6-tetrahydropyridazine, 1-(4-(pyrimidine-2-carbonylamino)benzoyl)-3-(3-cyclopentyloxy-4-methoxyphenyl)-1,4,5,6-tetrahydropyridazine, 1-(3-(pyrimidine-2-carbonylamino)benzoyl)-3-(3-cyclopentyloxy-4-methoxyphenyl)-1,4,5,6-tetrahydropyridazine, 1-(4-(pyrimidine-2-carbonylamino)benzoyl)-3-(3,4-methylenedioxyphenyl)-1,4,5,6-tetrahydropyridazine, 1-(4-(pyrimidine-2-carbonylamino)benzoyl)-3-(3-methoxy-4-methylsulfonylphenyl)-1,4,5,6-tetrahydropyridazine, 1-(4-(pyrimidine-2-carbonylamino)benzoyl)-3-(3-trifluoromethoxy-4-methoxyphenyl)-1,4,5,6-tetrahydropyridazine.

The compounds which follow are obtained analogously by reacting the "amine derivatives" listed above with pyrimidine-4-carbonyl chloride:

1-(4-(pyrimidine-4-carbonylamino)benzoyl)-3-(3,4-dimethoxyphenyl)-1,4,5,6-tetrahydropyridazine, m.p. 196°;

1-(3-(pyrimidine-4-carbonylamino)benzoyl)-3-(3,4-dimethoxyphenyl)-1,4,5,6-tetrahydropyridazine, 1-(2-(pyrimidine-4-carbonylamino)benzoyl)-3-(3,4-dimethoxyphenyl)-1,4,5,6-tetrahydropyridazine, 1-(4-(pyrimidine-4-carbonylamino)benzoyl)-3-(3-ethoxy-4-methoxyphenyl)-1,4,5,6-tetrahydropyridazine, 1-(3-(pyrimidine-4-carbonylamino)benzoyl)-3-(3-ethoxy-4-methoxyphenyl)-1,4,5,6-tetrahydropyridazine, 1-(4-(pyrimidine-4-carbonylamino)benzoyl)-3-(3-cyclopentyloxy-4-methoxyphenyl)-1,4,5,6-tetrahydropyridazine, 1-(3-(pyrimidine-4-carbonylamino)benzoyl)-3-(3-cyclopentyloxy-4-methoxyphenyl)-1,4,5,6-tetrahydropyridazine, 1-(4-(pyrimidine-4-carbonylamino)benzoyl)-3-(3,4-methylenedioxyphenyl)-1,4,5,6-tetrahydropyridazine, 1-(4-(pyrimidine-4-carbonylamino)benzoyl)-3-(3-methoxy-4-methylsulfonylphenyl)-1,4,5,6-tetrahydropyridazine, 1-(4-(pyrimidine-4-carbonylamino)benzoyl)-3-(3-trifluoromethoxy-4-methoxyphenyl.

The compounds which follow further below are obtained analogously by reacting 1-(4-aminobenzylcarbonyl)-3-(3,4-dimethoxyphenyl)-1,4,5,6-tetrahydropyridazine, 1-(3-aminobenzylcarbonyl)-3-(3,4-dimethoxyphenyl)-1,4,5,6-tetrahydropyridazine, 1-(2-aminobenzylcarbonyl)-3-(3,4-dimethoxyphenyl)-1,4,5,6-tetrahydropyridazine, 1-(4-aminobenzylcarbonyl)-3-(3-ethoxy-4-methoxyphenyl)-1,4,5,6-tetrahydropyridazine, 1-(3-aminobenzylcarbonyl)-3-(3-ethoxy-4-methoxyphenyl)-1,4,5,6-tetrahydropyridazine, 1-(4-aminobenzylcarbonyl)-3-(3-cyclopentyloxy-4-methoxyphenyl)-1,4,5,6-tetrahydropyridazine, 1-(3-aminobenzylcarbonyl)-3-(3-cyclopentyloxy-4-methoxyphenyl)-1,4,5,6-tetrahydropyridazine, 1-(4-aminobenzylcarbonyl)-3-(3,4-methylenedioxyphenyl)-1,4,5,6-tetrahydropyridazine, 1-(4-aminobenzylcarbonyl)-3-(3-methoxy-4-methylsulfonylphenyl)-1,4,5,6-t-trahydropyridazine, 1-(4-aminobenzylcarbonyl)-3-(3-trifluoromethoxy-4-methoxyphenyl)-1,4,5,6-tetrahydropyridazine, with nicotinoyl chloride:

1-(4-nicotinoylaminobenzylcarbonyl)-3-(3,4-dimethoxyphenyl)-1,4,5,6-tetrahydropyridazine hydrochloride, m.p. 225°;

1-(3-nicotinoylaminobenzylcarbonyl)-3-(3,4-dimethoxyphenyl)-1,4,5,6-tetrahydropyridazine, 1-(2-nicotinoylaminobenzylcarbonyl)-3-(3,4-dimethoxyphenyl)-1,4,5,6-tetrahydropyridazine, 1-(4-nicotinoylaminobenzylcarbonyl)-3-(3-ethoxy-4-methoxyphenyl)-1,4,5,6-tetrahydropyridazine, 1-(3-nicotinoylaminobenzylcarbonyl)-3-(3-ethoxy-4-methoxyphenyl)-1,4,5,6-tetrahydropyridazine, 1-(4-nicotinoylaminobenzylcarbonyl)-3-(3-cyclopentyloxy-4-methoxyphenyl)-1,4,5,6-tetrahydropyridazine, 1-(3-nicotinoylaminobenzylcarbonyl)-3-(3-cyclopentyloxy-4-methoxyphenyl)-1,4,5,6-tetrahydropyridazine, 1-(4-nicotinoylaminobenzylcarbonyl)-3-(3,4-methylenedioxyphenyl)-1,4,5,6-tetrahydropyridazine, 1-(4-nicotinoylaminobenzylcarbonyl)-3-(3-methoxy-4-methylsulfonylphenyl)-1,4,5,6-tetrahydropyridazine, 1-(4-nicotinoylaminobenzylcarbonyl)-3-(3-trifluoromethoxy-4-methoxyphenyl)-1,4,5,6-tetrahydropyridazine.

The following are obtained analogously by reacting 1-(4-aminobenzylcarbonyl)-3-(3,4-dimethoxyphenyl)-1,4,5,6-tetrahydropyridazine with isonicotinoyl chloride:

1-(4-isonicotinoylaminobenzylcarbonyl)-3-(3,4-dimethoxyphenyl)-1,4,5,6-tetrahydropyridazine hydrochloride, m.p. 209° C. and with ethyl chloroformate 1-(4-ethoxycarbonylaminobenzylcarbonyl)-3-(3,4-dimethoxyphenyl)-1,4,5,6-tetrahydropyridazine, m.p. 143°.

EXAMPLE 3

A solution of 2.0 g of 1-(4-aminobenzoyl)-3-(3,4-dimethoxyphenyl)-1,4,5,6-tetrahydropyridazine, m.p. 197°, and 0.8 ml of pyridine in 160 ml of dichloromethane is treated with 0.6 ml of ethyl chloroformate ("B") and stirring is continued for 2 hours. The solvent is removed and the residue is worked up as customary. After recrystallization from isopropanol/petroleum ether, 2.2 g of 1-(4-ethoxycarbonylaminobenzoyl)-3-(3,4-dimethoxyphenyl)-1,4,5,6-tetrahydropyridazine, m.p. 165°, are obtained.

The compounds which follow further below are obtained analogously by reacting the "amine derivatives" which follow 1-(3-aminobenzoyl)-3-(3,4-dimethoxyphenyl)-1,4,5,6-tetrahydropyridazine, 1-(2-aminobenzoyl)-3-(3,4-dimethoxyphenyl)-1,4,5,6-tetrahydropyridazine, 1-(4-aminobenzoyl)-3-(3-ethoxy-4-raethoxyphenyl)-1,4,5,6-tetrahydropyridazine, 1-(3-aminobenzoyl)-3-(3-ethoxy-4-methoxyphenyl)-1,4,5,6-tetrahydropyridazine, 1-(4-aminobenzoyl)-3-(3-cyclopentyloxy-4-methoxyphenyl)-1,4,5,6-tetrahydropyridazine, 1-(3-aminobenzoyl)-3-(3-cyclopentyloxy-4-methoxyphenyl)-1,4,5,6-tetrahydropyridazine, 1-(4-aminobenzoyl)-3-(3,4-methylenedioxyphenyl)-1,4,5,6-tetrahydropyridazine, 1-(4-aminobenzoyl)-3-(3-methoxy-4-methylsulfonylphenyl)-1,4,5,6-tetrahydropyridazine, 1-(4-aminobenzoyl)-3-(3-trifluoromethoxy-4-methoxyphenyl)-1,4,5,6-tetrahydropyridazine, with "B":

1-(3-ethoxycarbonylaminobenzoyl)-3-(3,4-dimethoxyphenyl)-1,4,5,6-tetrahydropyridazine, m.p. 181°;

1-(2-ethoxycarbonylaminobenzoyl)-3-(3,4-dimethoxyphenyl)-1,4,5,6-tetrahydropyridazine, 1-(4-ethoxycarbonylaminobenzoyl)-3-(3-ethoxy-4-methoxyphenyl)-1,4,5,6-tetrahydropyridazine, m.p. 147°;

1-(3-ethoxycarbonylaminobenzoyl)-3-(3-ethoxy-4-methoxyphenyl)-1,4,5,6-tetrahydropyridazine, 1-(4-ethoxycarbonylaminobenzoyl)-3-(3-cyclopentyloxy-4-methoxyphenyl)-1,4,5,6-tetrahydropyridazine, m.p. 1660;

1-(3-ethoxycarbonylaminobenzoyl)-3-(3-cyclopentyloxy-4-methoxyphenyl)-1,4,5,6-tetrahydropyridazine, 1-(4-ethoxycarbonylaminobenzoyl)-3-(3,4-methylenedioxyphenyl)-1,4,5,6-tetrahydropyridazine, 1-(4-ethoxycarbonylaminobenzoyl)-3-(3-methoxy-4-methylsulfonylphenyl)-1,4,5,6-tetrahydropyridazine, 1-(4-ethoxycarbonylaminobenzoyl)-3-(3-trifluoromethoxy-4-methoxyphenyl)-1,4,5,6-tetrahydropyridazine.

The compounds which follow are obtained analogously with the "amine derivatives" listed above and with methyl chloroformate:

1-(4-methoxycarbonylaminobenzoyl)-3-(3,4-dimethoxyphenyl)-1,4,5,6-tetrahydiopyridazine, m.p. 226°;

1-(3-methoxycarbonylaminobenzoyl)-3-(3,4-dimethoxyphenyl)-1,4,5,6-tetrahydropyridazine, 1-(2-methoxycarbonylaminobenzoyl)-3-(3,4-dimethoxyphenyl)-1,4,5,6-tetrahydropyridazine, 1-(4-methoxycarbonylaminobenzoyl)-3-(3-ethoxy-4-methoxyphenyl)-1,4,5,6-tetrahydropyridazine, 1-(3-methoxycarbonylaminobenzoyl)-3-(3-ethoxy-4-methoxyphenyl)-1,4,5,6-tetrahydropyridazine, 1-(4-methoxycarbonylaminobenzoyl)-3-(3-cyclopentyloxy-4-methoxyphenyl)-1,4,5,6-tetrahydropyridazine, 1-(3-methoxycarbonylaminobenzoyl)-3-(3-cyclopentyloxy-4-methoxyphenyl)-1,4,5,6-tetrahydropyridazine, 1-(4-methoxycarbonylaminobenzoyl)-3-(3,4-methylenedioxyphenyl)-1,4,5,6-tetrahydropyridazine, 1-(4-methoxycarbonylaminobenzoyl)-3--(3-methoxy-4-methylsulfonylphenyl)-1,4,5,6-tetrahydropyridazine.

1-(4-methoxycarbonylaminobenzoyl)-3-(3-trifluoromethoxy-4-methoxyphenyl)-1,4,5,6-tetrahydropyridazine.

The compounds which follow are obtained analogously with the "amine derivatives" listed above and with acetyl chloride:

1-(4-acetamidobenzoyl)-3-(3,4-dimethoxyphenyl)-1,4,5,6-tetrahydropyridazine, m.p. 230°;

1-(3-acetamidobenzoyl)-3-(3,4-dimethoxyphenyl)-1,4,5,6-tetrahydropyridazine, 1-(2-acetamidobenzoyl)-3-(3,4-dimethoxyphenyl)-1,4,5,6-tetrahydropyridazine, 1-(4-acetamidobenzoyl)-3-(3-ethoxy-4-methoxyphenyl)-1,4,5,6-tetrahydropyridazine, 1-(3-acetamidobenzoyl)-3-(3-ethoxy-4-methoxyphenyl)-1,4,5,6-tetrahydropyridazine, 1-(4-acetamidobenzoyl)-3-(3-cyclopentyloxy-4-methoxyphenyl)-1,4,5,6-tetrahydropyridazine, 1-(3-acetamidobenzoyl)-3-(3-cycloentyloxy-4-methoxyphenyl)-1,4,5,6-tetrahydropyridazine, 1-(4-acetamidobenzoyl)-3-(3,4-methylenedioxyphenyl)-1,4,5,6-tetrahydropyridazine, 1-(4-acetamidobenzoyl)-3-(3-methoxy-4-methylsulfonylphenyl)-1,4,5,6-tetrahydropyridazine, 1-(4-acetamidobenzoyl)-3-(3-trifluoromethoxy-4-methoxyphenyl)-1,4,5,6-tetrahydropyridazine.

EXAMPLE 4

A solution of 2.0 g of 1-(4-aminobenzoyl)-3-(3,4-dimethoxyphenyl)-1,4,5,6-tetrahydropyridazine and 0.8 ml of N-ethyl isocyanate in 160 ml of dichloromethane is stirred for two hours at room temperature. The solvent is removed and the residue is worked up as customary. After recrystallization from isopropanol/petroleum ether, 2.1 g of 1-(4-ethylureidobenzoyl)-3-(3,4-dimethoxyphenyl)-1,4,5,6-tetrahydropyridazine are obtained.

Analogously, by reacting with potassium cyanate the following compound is obtained 1-(4-ureidobenzoyl)-3-(3-ethoxy-4-methoxyphenyl)-1,4,5,6-tetra-hydropyridazine, m.p. 251°.

EXAMPLE 5

Analogously to the Examples 2 and 3 the following compounds are obtained 1-(4-nicotinoylaminobenzoyl)-3-(3-propoxy-4-methoxyphenyl)-1,4,5,6-tetrahydropyridazine, m.p. 239°;

1-(4-trifluoroacetamidobenzoyl)-3-(3-ethoxy-4-methoxyphenyl)-1,4,5,6-tetrahydropyridazine, m.p. 211°;

1-(4-ethoxycarbonylaminobenzoyl)-3-(3-propoxy-4-methoxy-phenyl)-1,4,5,6-tetrahydropyriciazine, m.p. 154°;

1-(4-isopropoxycarbonylaminobenzoyl)-3-(3-ethoxy-4-methoxy-phenyl)-1,4,5,6-tetrahydropyridazine, m.p. 147°;

1-(4-propoxycarbonylaminobenzoyl)-3-(3-ethoxy-4-methoxy-phenyl)-1,4,5,6-tetrahydropyridazine, m.p. 113°.

EXAMPLE 6

Analogously to the Examples 2 and 3 the following compounds are obtained by reaction of 1-(4-aminobenzoyl)-3-(3,4-dimethoxyphenyl)-4-methyl-1,4,5,6-tetrahydropyridazine with nicotinoylchloride 1-(4-nicotinoylaminobenzoyl)-3-(3,4-dimethoxyphenyl)-4-methyl-1,4,5,6-tetrahydropyridazine, m.p. 190°;

with "B"

1-(4-ethoxycarbonylaminobenzoyl)-3-(3,4-dimethoxyphenyl)-4-methyl-1,4,5,6-tetrahydropyridazine, m.p. 141°;

with acetyl cloride 1-(4-acetamidobenzoyl)-3-(3,4-dimethoxy-phenyl)-4-methyl-1,4,5,6-tetrahydropyridazine, m.p. 223°.

The examples which follow relate to pharmaceutical products:

Example A: Vials

A solution of 100 g of an active ingredient of the formula I and 5 g of disodium hydrogen phosphate in 3 l of twice-distilled water is brought to pH 6.5 with 2N hydrochloric acid, filter-sterilized, filled into vials, lyophilized under sterile conditions and sealed in sterile form. Each vial comprises 5 mg of active ingredient.

Example B: Suppositories

A mixture of 20 g of an active ingredient of the formula I is melted with 100 g of soya lecithin and 1400 g of cocoa butter, and the mixture is poured into moulds and left to cool. Each suppository comprises 20 mg of active ingredient.

Example C: Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of twice-distilled water. The pH is brought to 6.8, and the solution is made up to 1 l and sterilized by irradiation. This solution can be used in the form of eyedrops.

Example D: Ointment 500 mg of an active ingredient of the formula I are mixed with 99.5 g of petroleum jelly under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is tableted in the customary manner in such a way that each tablet comprises 10 mg of active ingredient.

Example F: Sugar-Coated Tablets

A mixture is tableted analogously to Example E, and the tablets are subsequently coated in the customary manner with a coating of sucrose, potato starch, talc, tragacanth and colouring.

Example G: Capsules 2 kg of active ingredient of the formula I are filled into hard gelatin capsules in the customary manner so that each capsule comprises 20 mg of the active ingredient.

Example H: Ampoules

A solution of 1 kg of active ingredient of the formula I in 60 l of twice-distilled water is filter-sterilized, filled into ampoules, lyophilized under sterile conditions and sealed in sterile form. Each ampoule comprises 10 mg of active ingredient.

Example I: Spray for Inhalation 14 g of active ingredient of the formula I are dissolved in 10 l of isotonic NaCl solution, and the solution is filled into commercially available pump-operated spray containers. The solution can be sprayed into mouth or nose. One actuation (approximately 0.1 ml) corresponds to a dose of approximately 0.14 mg.

What is claimed is:

1. A compound of the formula I

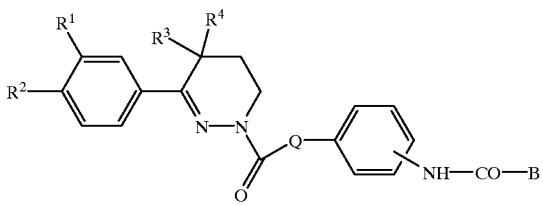

in which
- B is A, OA, NH$_2$, NHA, NAA' or an unsaturated heterocycle which has 1 to 4 N, O and/or S atoms and which is optionally unsubstituted or mono-, di- or trisubstituted by Hal, A and/or OA,
- Q is absent or is alkylene having 1–6 C atoms,
- R$^1$, R$^2$ in each case independently of one another are —OH, OR$^5$, —S—R$^5$, —SO—R$^5$, —SO$_2$—R$^5$, Hal, —NO$_2$, —NH$_2$, —NHR$^5$ or —NR$^5$R$^6$,
- R$^1$ and R$^2$ together are also —O—CH$_2$—O—,
- R$^3$, R$^4$ in each case independently of one another are H or A,
- R$^5$, R$^6$ in each case independently of one another are A, cycloalkyl having 3–7 C atoms, methylenecycloalkyl having 4–8 C atoms or alkenyl having 2–8 C atoms,
- A, A' in each case independently of one another are alkyl which has 1 to 10 C atoms and which can be substituted by 1 to 5 F and/or Cl atoms and
- Hal is F, Cl, Br or I, or a physiologically acceptable salt or enantiomer thereof.

2. An enantiomer of a compound of the formula I according to claim 1.

3. A compound of the formula I according to claim 1, which is selected from the group consisting of
    (a) 1-(4-nicotinoylaminobenzoyl)-3-(3-ethoxy-4-methoxyphenyl)-1,4,5,6-tetrahydropyridazine;
    (b) 1-(4-ethoxycarbonylaminobenzoyl)-3-(3-ethoxy-4-methoxyphenyl)-1,4,5,6-tetrahydropyridazine;
    (c) 1-(4-nicotinoylaminobenzoyl)-3-(3-cyclopentyloxy-4-methoxyphenyl)-1,4,5,6-tetrahydropyridazine;
    (d) 1-(4-ethoxycarbonylaminobenzoyl)-3-(3-cyclopentyloxy-4-methoxyphenyl)-1,4,5,6-tetrahydropyridazine;
    (e) 1-(4-isonicotinoylaminobenzoyl)-3-(3-ethoxy-4-methoxyphenyl)-1,4,5,6-tetrahydropyridazine;
    (f) 1-(4-isonicotinoylaminobenzoyl)-3-(3-cyclopentyloxy-4-methoxyphenyl)-1,4,5,6-tetrahydropyridazine;
    (g) 1-(4-nicotinoylaminobenzoyl)-3-(3,4-dimethoxyphenyl)-1,4,5,6-tetrahydropyridazine; and
    (h) 1-(4-ethoxycarbonylaminobenzoyl)-3-(3,4-dimethoxyphenyl)-1,4,5,6-tetrahydropyridazine.

4. A compound of the formula I of claim 1 or a physiologically acceptable salt or enantiomer thereof, wherein
- R$^1$ and R$^2$ are in each case independently of one another OA,
- Q is absent, and
- B is pyridinyl, pyrazinyl, pyrimidinyl, thiazolyl, imidazolyl or isoxazolyl.

5. A compound of the formula I of claim 1 or a physiologically acceptable salt or enantiomer thereof, wherein
- R$^1$ and R$^2$ are in each case independently of one another OA,
- Q is methylene, and
- B is pyridinyl, pyrazinyl, pyrimidinyl, thiazolyl, imidazolyl or isoxazolyl.

6. A compound of the formula I of claim 1 or a physiologically acceptable salt or enantiomer thereof, wherein
- R1 and R$^2$ together are —O—CH$_2$—O—,
- Q is absent or alkylene with 1–6 C atoms, and
- B is pyridinyl, pyrazinyl, pyrimidinyl, thiazolyl, imidazolyl or isoxazolyl.

7. A compound of the formula I of claim 1 or a physiologically acceptable salt or enantiomer thereof, wherein
- R$^1$ and R$^2$ are in each case independently of one another OA,
- Q is absent or alkylene with 1–6 C atoms, and
- B is A or OA.

8. A compound of the formula I of claim 1 or a physiologically acceptable salt or enantiomer thereof, wherein
- R$^1$ and R$^2$ are in each case independently of one another OA,
- Q is absent or alkylene with 1–6 C atoms,
- B is pyridinyl, pyrazinyl, pyrimidinyl, thiazolyl, imidazolyl, isoxazolyl, A, OA or NH$_2$.

9. A process for the preparation of a compound of the formula I according to claim 1 or a salt or enantiomer thereof, comprising:

reacting a compound of the formula II

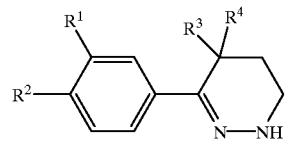

in which R$^1$ and R$^2$ have the abovementioned meanings with a compound of the formula III

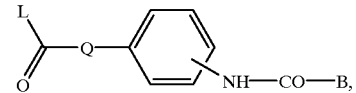

in which
B and Q have the abovementioned meanings and
L is Cl, Br, OH or a reactive esterified OH group, or
reacting a compound of the formula IV

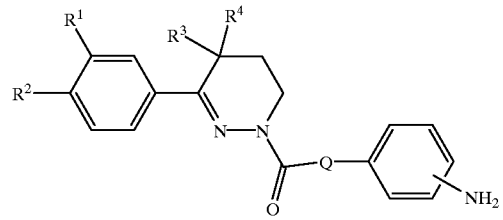

in which

R$^1$, R$^2$ and Q have the abovementioned meanings with a compound of formula V $$B-CO-L \quad \quad V$$

in which

B has the abovementioned meaning and

L is Cl, Br, OH or a reactive esterified OH group, and/or converting a basic compound of the formula I is into a salt thereof by treatment with an acid.

10. The process of claim 9, wherein the process comprises reacting a compound of the formula II with a compound of the formula III and L in formula III is Cl, Br, OH or reactive esterified group selected from the group consisting of alkylsulfonyloxy having 1–6 C atoms and arylsulfonyloxy having 6–10 C atoms.

11. A process for preparing a pharmaceutical composition, comprising bringing a compound of the formula I according to claim 1 and/or a physiologically acceptable salt thereof into a suitable pharmaceutical form together with at least one solid, liquid or semi-liquid excipient or auxiliary.

12. A pharmaceutical composition which comprises at least one compound of the formula I according to claim 1 and/or a physiologically acceptable salt thereof.

13. A pharmaceutical composition according to claim 12, which comprises an amount of the compound of the formula I and/or a physiologically acceptable salt thereof effective for phosphodiesterase IV inhibiting activity.

14. A pharmaceutical composition according to claim 12, which comprises the compound of formula I and/or a physiologically acceptable salt thereof in a dose of from 1 to 500 mg.

* * * * *